United States Patent [19]
Dunkel et al.

[11] Patent Number: 5,306,497
[45] Date of Patent: Apr. 26, 1994

[54] INSECTICIDAL OR INSECT BEHAVIORALLY ACTIVE PREPARATIONS FROM AROMATIC PLANTS

[75] Inventors: Florence V. Dunkel, Bozeman, Mont.; David K. Weaver, Nova Scotia, Canada; Weaver, III: Theodore W., Bozeman, Mont.

[73] Assignee: Research and Development Institute Inc. at Montana State University, Bozeman, Mont.

[21] Appl. No.: 801,817

[22] Filed: Dec. 6, 1991

[51] Int. Cl.$^5$ .............................................. A01N 65/00
[52] U.S. Cl. ........................ 424/195.1; 424/DIG. 10; 514/919
[58] Field of Search .................... 424/195.1, DIG. 10; 514/919

[56] References Cited

PUBLICATIONS

Weaver et al, J. Stored Prod. Res., vol. 27, No. 4, "The Efficacy of Linalool, A Major Component of Freshly-Milled *Ocimum canum* Sims (Lamiaceae), For Protection Against Postharvest Damage by Certain Stored Product Coleoptera", pp. 213-220, 1991.
Lambert et al, Insect Science Applications, vol. 6, No. 2, "Bruchid Control With Traditionally Used Insecticdal Plants *Hyptis spicigera* and *Cassia nigricans*", pp. 167-170, 1985.
Su, Journal of Economic Entomology, vol. 70, No. 1, "Insecticidal Properties of Black Pepper to Rice Weevils1 and Cowpea Weevils2,3,4", pp. 18-21 1977.
Chem. Abst. 111: 28406w, 1989.
Chem. Abst. 106: 153062d, 1987.
Lew, W. Medical Botany, Wley & Sons, New York, p. 286, 1977.
McIndoo, N. E., Plants of Possible Insecticidal Value, USDA, 1945, pp. 36, 134-136.
Dixit, R. S. Indigenous Insecticides. P. III. Insecticidal Properties of Some Medicinal and Aromatic Plants, pp. 169-172, 1963.

*Primary Examiner*—John W. Rollins
*Attorney, Agent, or Firm*—Lowe, Price, LeBlanc & Becker

[57] ABSTRACT

Preparations from aromatic plants that are insecticidal or are insect behaviorally active, are used to control the development of insect populations. The plants are harvested after leaf maturation. Leaves are removed in a random pattern both as to individual plants and to location of leaves on each plant. The collection includes petioles but not stems. Leaves are milled with or without drying to a small average particle size. Extracts and vapors may also be used. The resultant preparation, when contacted with dry commodities infested with storage insects or with insect infested perishable produce after harvest will reduce the insect population.

9 Claims, 4 Drawing Sheets

5,306,497

INSECTICIDAL OR INSECT BEHAVIORALLY ACTIVE PREPARATIONS FROM AROMATIC PLANTS

FIELD OF THE INVENTION

The present invention involves a new approach to obtain and manufacture natural insecticidal or insect behaviorally active materials from aromatic plants. Mote particularly, the invention provides a new approach to control insects from renewable non-petroleum sources.

BACKGROUND OF THE INVENTION

Many procedures are known in the prior art and commercially for insect control. The procedures commonly relied on involve treatment of the insect with a toxic substance such as a synthetic chemical including the use of petroleum-based chemicals which raise substantial environmental and health problems. The art continues to search for products and processes which will enable man to effectively control insects or modify their behavior. The present invention meets this need.

DISCLOSURE OF THE INVENTION

It is accordingly an object of the present invention to provide plant based insect control preparations for insect management and control.

A further object of the present invention is to provide a method for the preparation of substances from aromatic plants which are useful to control unwanted or noxious insects or modify their behavior.

A still further object of the present invention is to provide insecticidal compositions which are produced from natural plants and which are effective to manage or control insects or modify their behavior.

Other objects and advantages of the present invention will become obvious as the description thereof proceeds.

In satisfaction of the foregoing objects and advantages, the present invention provides an insecticidal composition prepared from aromatic plants which are lethal to insects or are effective to control insect behavior by controlling the development of insect populations. The compositions of the invention are prepared from plants which are harvested after leaf maturation, and then milled to a small particle size. The resulting product is then combined with dry commodities infested with storage insects, insect-infested perishable produce after harvest, or used to fumigate the soil. These compositions are new sources of materials for insect management which do not involve the use of petroleum-based chemicals.

BRIEF DESCRIPTION OF THE DRAWINGS

Reference is now made to the drawings accompanying this application, wherein.

DESCRIPTION OF PREFERRED EMBODIMENTS

Figure 1:
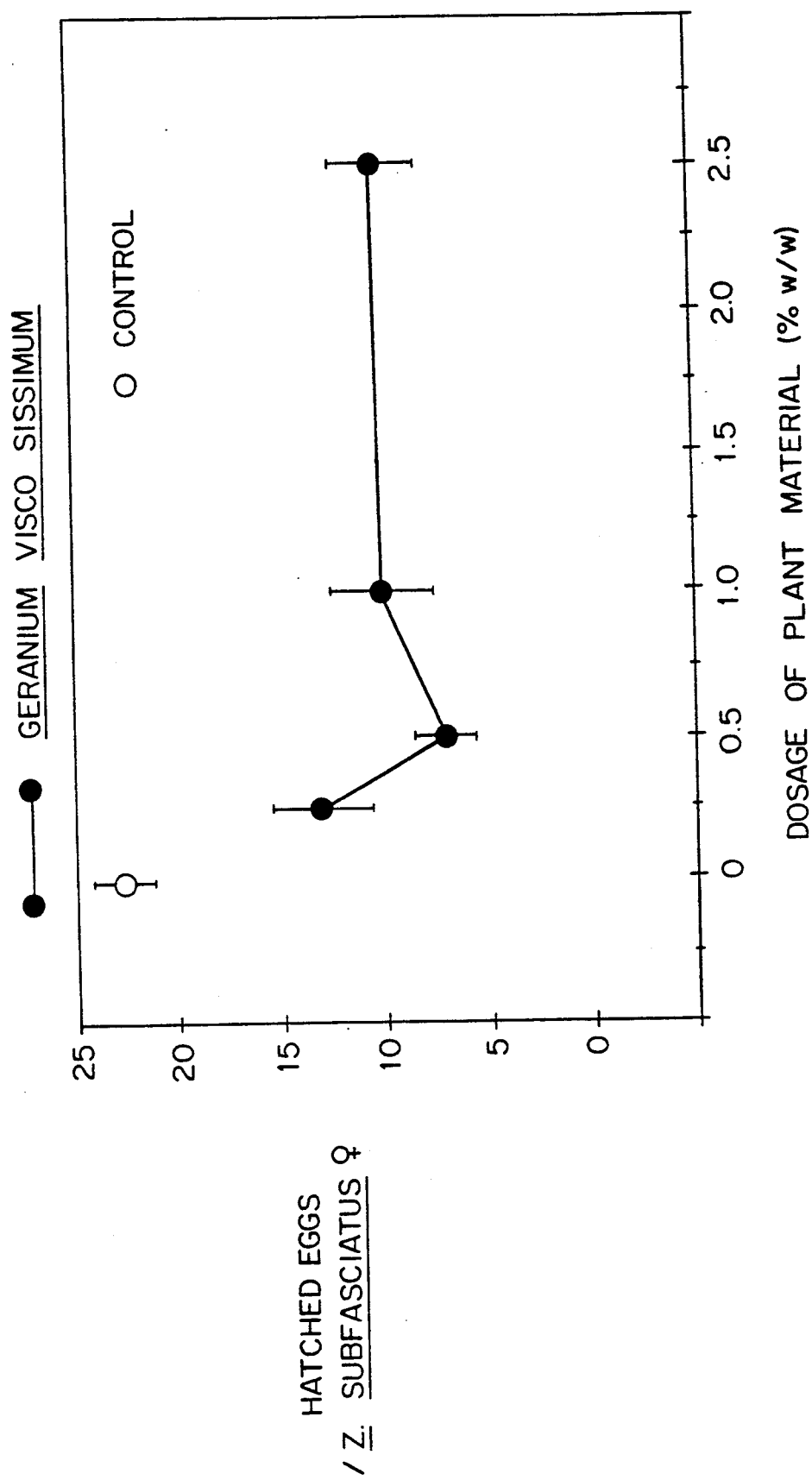
FIGS. 1, 2, 3, and 4 are graphs which demonstrate the effect on the number of hatched eggs of the insect *Z. subfasciatus* with respect to four different species of plants of this invention.

The present invention is concerned with a new approach to insect control and management and provides methods for reducing insect populations and/or control of insect behavior. The present invention represents a significant step in this art since it is not based on the use of petroleum-based chemicals, non-renewable resources or imported resources and therefore, does not present hazards to health and the environment. The invention is based on the recognition that certain plants which are aromatic in nature can be processed to provide an insect control composition or preparation.

The present invention is based on the use of aromatic plants which are insecticidal or insect behaviorally active and which can be processed to a form which will be effective to be lethal to insects or to control the development of insect populations. The invention is considered to be broadly applicable to any plant which has the necessary characteristics for insect management or control. Aromatic plants are particularly useful with plants of the mint family being preferred. In this invention, the compositions and methods are demonstrated by the use of five different aromatic plants defined herein below by common name and scientific name:

1. Sticky Geranium, *Geranium viscosissimum;*
2. Balsam Root, *Balsamorhiza sagittata;*
3. Sagebrush, *Artemesia tridentata;*
4. African Mint, *Ocimum canum;*
5. Bergamot's Mint or Horse Mint, *Monarda fistulosa*

While these five species have been found useful in the invention, it is considered that many other plants and especially aromatic plants are useful in accordance with the methods described in this invention. Therefore, these examples are not construed in any way to be limiting to the invention with respect to the plants disclosed.

The compositions of the present invention are particularly useful in insect control in closed environments such as in packing cases or for stored commodities and the like. The compositions of the present invention are also useful in soil fumigation. In use, preparations of the composition are introduced into the packing cases or in contact with the stored commodities where insects are often a problem. In soil fumigation, the composition is introduced into the soil or the soil is coated with the composition. The amount of composition used will vary with the insect infestation present or expected but should range from about 0.1 to 99 wt. %, preferably 0.25 to 10 wt. % of the material being protected. Since the composition of this invention is not toxic, nor a threat to the environment, the amount to be used is not critical.

In accordance with this invention, the insects will be destroyed or killed directly or the reproduction abilities of the insects will be reduced.

The composition of the invention is prepared by harvesting leaves from the desired plant or mixture of different varieties in a random pattern while including petioles but not stem material. The collection or harvest is then dried either in bulk or in containers in an oven or the like to remove moisture. Heating in an oven at 95° F. to 150° F. for 1 to 5 hours is usually sufficient. The dried plant material is then milled preferably to a final average particle size which is about 2.0 $mm^2$ or smaller. It has been found as shown in the examples below that the smaller particle size increases the effectiveness of the composition.

In accordance with the invention, liquid extracts and vapors from the aromatic plants are also useful for insect control. For example, sagebrush vapors can be used effectively.

The resulting milled leaf tissue may then be added in a range of concentration as discussed above to the stored product to be protected or soil to be fumigated.

Mixing may be done by hand or by machine in a conventional manner.

It has been discovered that the plant material prepared in accordance with this invention is extremely effective in reducing insect concentrations and preventing their proliferation without risks to health or the environment. The composition of the invention is useful in insect control against a wide variety of insects including those found in the storage of commodities such as beans, potatoes, tomatoes, grains such as barley, wheat and corn. The composition of the invention is effective against the bean bruchid, fruit flies and the like.

The following examples are presented to illustrate the invention, but it is not considered to be limited thereto. In the examples, parts are by weight unless otherwise indicated.

EXAMPLE 1

Plant material was prepared by harvesting leaves in a random pattern both as to individual plants and to location of leaf on each plant. The collection included petioles by not stem material which was removed prior to drying. Leaves were placed in paper bags in the plant drying room at 125° F. for 72 hours. The plant material was then removed, cooled, and milled in a blender for 1.5 minutes. The final particle size was less than or equal to 2.0 mm$^2$. The preference for the precision of this size is further illustrated in Example 4 and Example 7. The milled leaf tissue was then added immediately in a range of concentrations, each in ten replications, to plastic vials containing the stored product to be protected and mixed by rotation as described in the following examples. For purposes of some bioassays, but not in actual practice, the milled material was also tested directly without the stored commodity.

EXAMPLE 2

The techniques in Example 1 were used with *Geranium viscosissimum*, *Balsamorhiza sagittata*, *Artemesia tridentata*, and *Monarda fistulosa* in dry pinto beans (*Phaseolus vulgaris*) to control the bean bruchid, *Zabrotes subfasciatus*. Ten replicates were made of four concentrations (weight of plant material/weight of dry beans) 0%, 0.25%, 0.5%, 1.0%, and 2.5%. Each vial was inoculated with five male and five female *Z. subfasciatus* 0–1 day after emergence from stock culture beans as adults. This experiment was maintained under the same conditions that test insects were reared in stock culture, 12:12::light:dark photoperiod, 65±5% Relative Humidity, and 27°±1° C. After 25 days, mean number of eggs laid per female were determined, and mean % of eggs hatched were determined.

EXAMPLE 3

Figure 2:
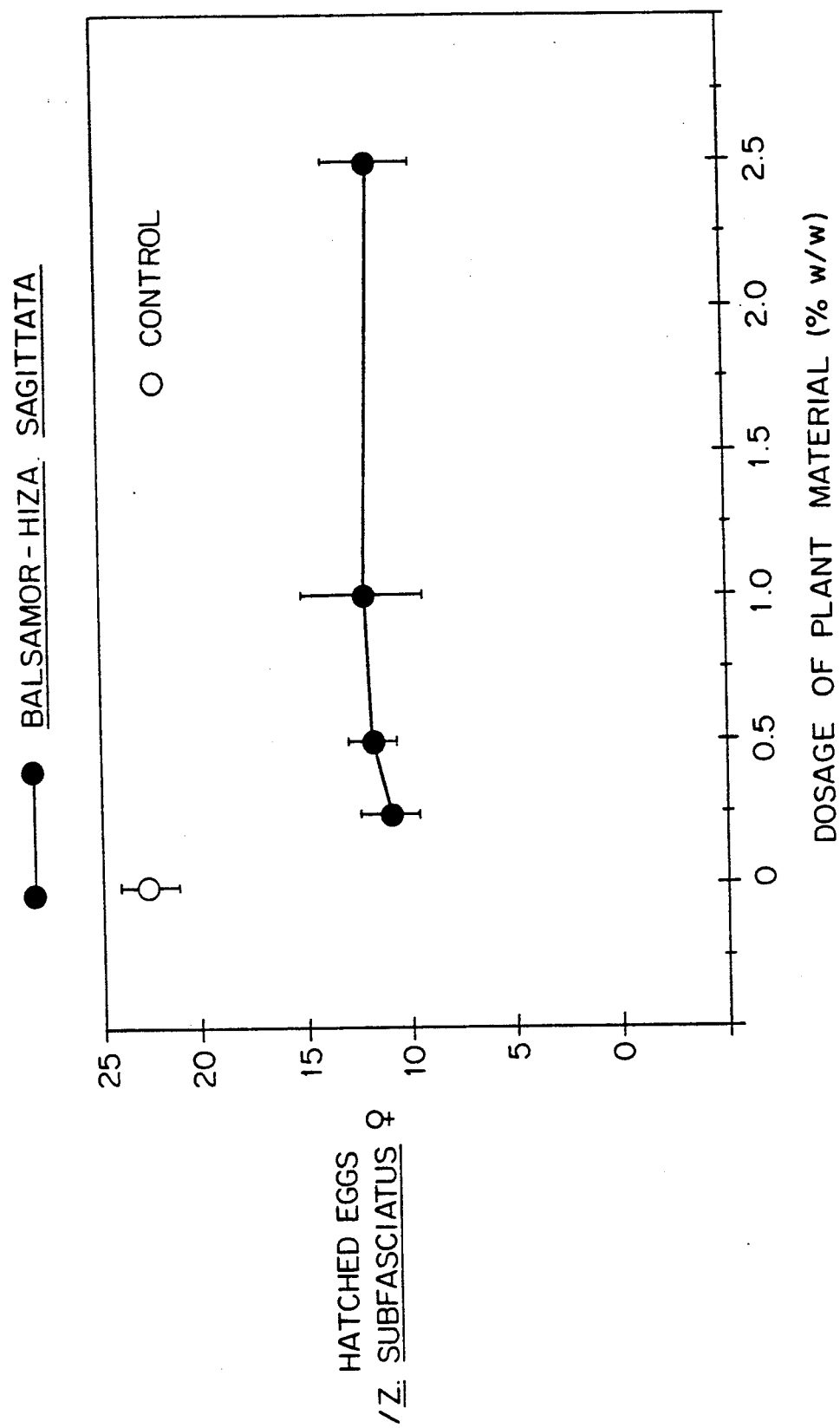
Figure 3:
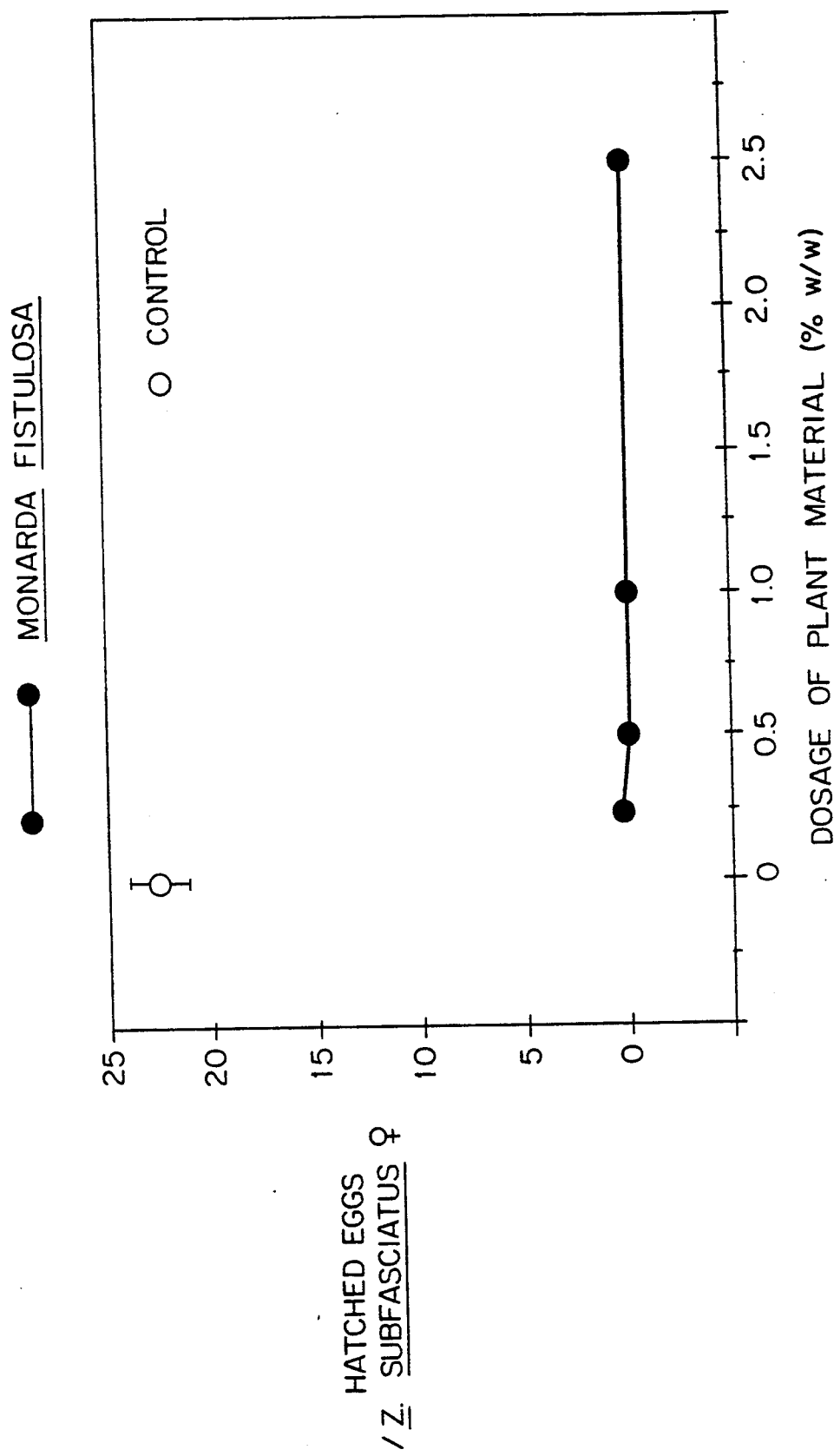
Figure 4:
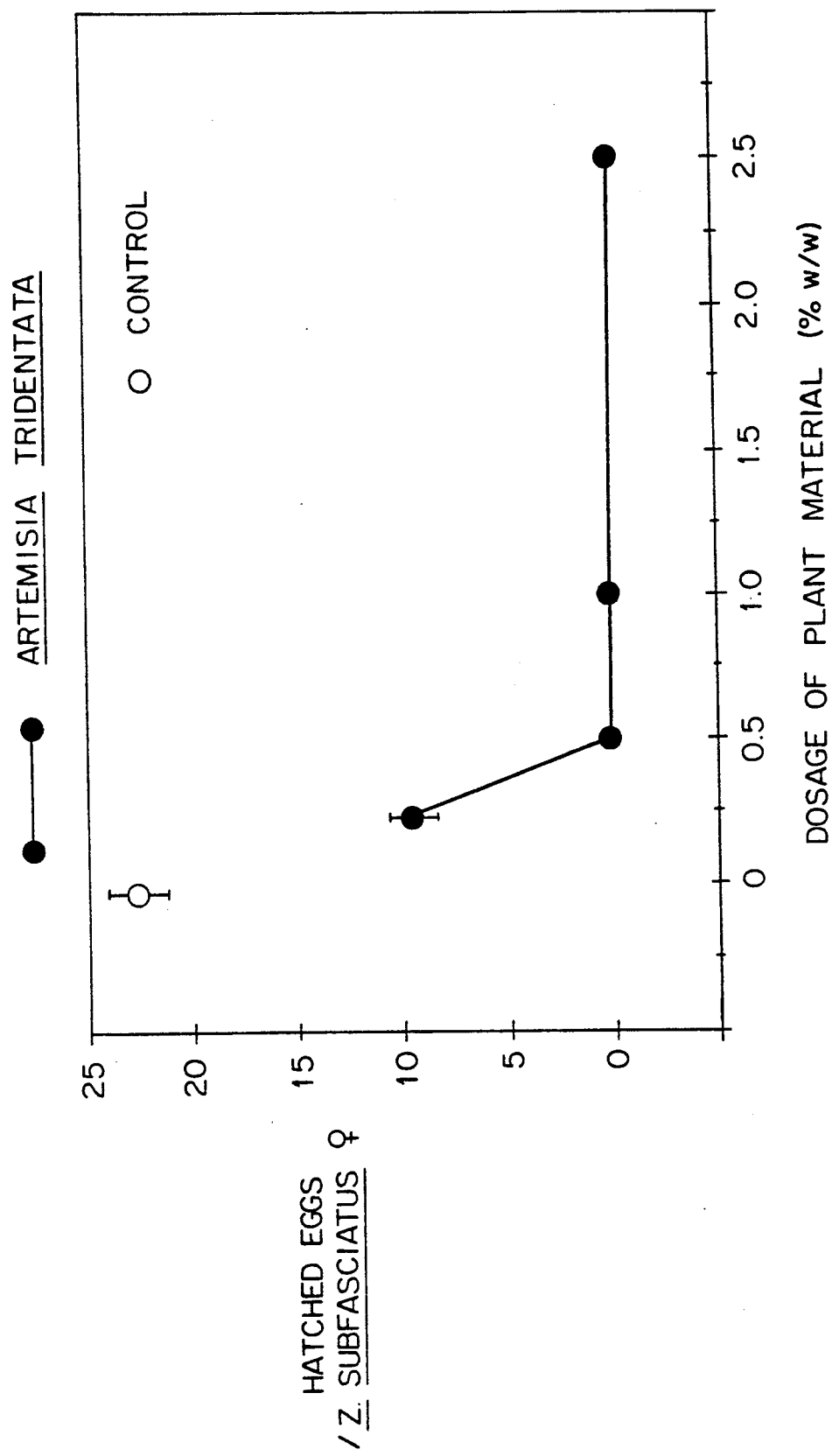

Using the techniques in Examples 1 and 2, the following results were obtained (refer to four attached graphs of FIGS. 1, 2, 3, and 4). The mean number of eggs laid by *Z. subfasciatus* were not significantly different from the mean number of eggs hatched per female for each of the plant preparations to which they were exposed. That is, regardless of the concentration, most of the eggs that were laid, subsequently hatched. Therefore, there is presented only the data for the eggs hatched per female. With *G. viscosissimum* and *B. sagittata* the hatched eggs per female was decreased by over half at concentrations of 0.5% or above in comparison to the control without any plant material. With *M. fistulosa*, there were no eggs hatched (and no eggs laid) at concentrations of 0.25% or above. With *A. tridentata*, there were no eggs hatched (or laid) at concentrations of 0.5% or above.

EXAMPLE 4

Trials were also run with *O. canum* whole vs. milled leaves with milled leaves that were larger than the claimed size which releases insecticidal compounds from the glandular hairs (trichomes). The bruchids *Acanthoscelides obtectus* and *Z. subfasciatus* were exposed to 1 g milled leaves mean size 2.0 to 5.0 mm$^2$ and to 1 g whole leaves of this mint plant. After 15 minutes, 84 of 100 adult *A. obtectus* were normal and 16 had difficulty walking. No abnormal response was obtained in the insects exposed to whole leaves or in similar chambers without any leaves. After 72 hours, 18 were dead in the coarsely milled replicates and 82 were normal. Similar results were obtained with *Z. subfasciatus*. With 1 g leaves of the same mint species milled to the size indicated in Example 1, 100% of the adult male *Z. subfasciatus* tested were dead after 24 hours and after 48 hours, 50% of the females were dead. There was no mortality in the controls.

EXAMPLE 5

Fumigation tests were conducted with two of the Rocky Mountain plants. Material prepared as described in Example 1 was placed in three concentrations (0, 0.1 g and 1.0 g) with three replicates in 42.5 ml glass vials. Insects were placed individually in smaller vials that were suspended in the larger vial. The covering of the smaller vial allowed sufficient gas exchange. Moribundity in 24 hours was followed by death in 72 hours with milled leaves of *A. tridentata* for 100% of the adult *Z. subfasciatus* tested. There were no moribund or dead individuals in either the 0 g or the 0.1 g concentrations. With the same experimental design, leaves of *M. fistulosa* were tested and found to cause moribundity in 100% of the adult *Z. subfasciatus* tested. 33% of the individuals in the 0.1 g concentration were moribund at 72 hours and dead at 120 hours.

EXAMPLE 6

Fumigation tests were also run with linalool, a known insecticidal component of leaves of *O. canum*, in similar small vials suspended within 42.5 ml glass vials, as used in Example 5. Similar results were obtained. The concentration of linalool released from 1 g of milled *O. canum* resulted in an LT50 of 15 hours for female *Z. subfasciatus*.

EXAMPLE 7

Vapors released from sagebrush, *A. tridentata*, reduced the development of fruit flies, *Drosophila melanogaster*, from eggs and reduced the fitness of resultant animals. The fruit flies resided in 200 ml bottles capped with cotton and partially filled (1 cm) with standard cornmeal-yeast medium. Fly development was compared in bottles containing a gauze bag containing nothing, sagebrush leaves (2 or 5 g samples), or crushed sagebrush leaves (prepared with a mortar and pestle to a particle size less than or equal to 1 mm2) (2 or 5 g samples). Three observations were made. 1) The percentage of eggs yielding adult flies declined with exposure to aromatic substances, while 76% of no-treatment animals reached adulthood and a similar 70–74% of individuals exposed to uncrushed leaves (2 g and 5 g) yielded adults, 10% fewer individuals survived exposure to crushed sagebrush (66 and 64% for 2 g and 5 g treatments, respectively). 2) Sage vapors had a lasting effect such that females exposed to sage vapors were less fit (i.e., saw fewer offspring to adulthood) than untreated females; females raised in sage vapors produced, in the absence of sage vapors, 43-60% (with 2 and 5 g samples) as many offspring as females raised in their absence. 3) The effect was aggravated, however, if the offspring were also raised in the presence of sage vapors; females raised in the presence of sage vapors raised 10-20% as many offspring in sage vapors as females raised in their absence.

From the foregoing examples, it will be seen that the invention is broadly applicable for the control and or management of various types of insects using plants as a control material. The plants may be used as bulk material in the form of milled dried leaves or extracts of liquids or vapors may also be used with corresponding results. It has been discovered unexpectedly according to the present invention that such materials have an adverse effect on insects particularly in controlled environments such as stored commodity packaging, soil fumigation and the like.

The foregoing descriptions are illustrative of the principles of the invention, with the key emphasis being the size of the milled particles. Numerous variations and modifications thereof would be apparent to the person skilled in the art. All such variations and modifications are to be considered to be within the spirit and scope of the invention.

What is claimed is:

1. A method for the control of insects in an environment by destruction or behavior modification which comprises:

preparing dried and finely milled leaves and mixtures thereof of one or more aromatic plants, wherein said plants are insecticidal or capable of modifying the behavior of insects, and adding said dried and finely milled leaves and mixtures thereof to said environment in an effective amount such that the insects are controlled by destruction or behavior modification, wherein said plants are aromatic plants selected from the group consisting of the mint family, *Geranium viscosissimum, Balsamorhiza sagittata, Artemesia tridentata* and mixtures thereof.

2. The method according to claim 1, wherein said plants are selected from the group consisting of *Ocimum canum, Monarda fistulosa* and mixtures thereof.

3. The method according to claim 1, wherein said environment comprises commodity storage areas and closed containers and said control of insects is by reduction in population.

4. The method according to claim 1, wherein said environment comprises soil.

5. A method according to claim 1, wherein the effective amount is 0.1 to 99 wt. % of the material being protected from the insects.

6. A method according to claim 1, wherein the leaves are milled to an average particle size of 1.0 mm$^2$ or smaller.

7. A method according to claim 1, wherein the insects are killed.

8. A method according to claim 1, wherein the reproduction abilities of the insects are reduced.

9. A method according to claim 1, wherein the insects are fruit flies and bean bruchid.

* * * * *